US008064991B2

(12) United States Patent
Hersh et al.

(10) Patent No.: US 8,064,991 B2
(45) Date of Patent: Nov. 22, 2011

(54) METHOD OF FETAL AND MATERNAL ECG IDENTIFICATION ACROSS MULTIPLE EPOCHS

(75) Inventors: Lawrence T. Hersh, Tampa, FL (US); Sai Kolluri, Tampa, FL (US); Bruce A. Friedman, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 989 days.

(21) Appl. No.: 11/970,553

(22) Filed: Jan. 8, 2008

(65) Prior Publication Data
US 2009/0177101 A1 Jul. 9, 2009

(51) Int. Cl.
*A61B 5/0444* (2006.01)
(52) U.S. Cl. .......................................... 600/511; 607/46
(58) Field of Classification Search .................. 600/511, 600/509, 546, 304
See application file for complete search history.

(56) References Cited

U.S. PATENT DOCUMENTS

| | | | |
|---|---|---|---|
| 5,372,139 A | 12/1994 | Holls et al. | |
| 2004/0243015 A1* | 12/2004 | Smith et al. | 600/511 |
| 2005/0267376 A1 | 12/2005 | Marossero et al. | |
| 2005/0267377 A1 | 12/2005 | Marossero et al. | |
| 2007/0066908 A1 | 3/2007 | Graupe et al. | |
| 2007/0233203 A1* | 10/2007 | Euliano et al. | 607/46 |

FOREIGN PATENT DOCUMENTS

| | | |
|---|---|---|
| EP | 1844706 A1 | 10/2007 |
| WO | 03028550 A2 | 4/2003 |
| WO | 04084087 A1 | 9/2004 |
| WO | 05039410 A1 | 5/2005 |
| WO | 05052848 A2 | 6/2005 |
| WO | 05117692 A2 | 12/2005 |
| WO | 09013246 A1 | 1/2009 |

OTHER PUBLICATIONS

GB Search Report dated Mar. 18, 2009.

* cited by examiner

*Primary Examiner* — Carl H. Layno
*Assistant Examiner* — Jon-Eric C. Morales
(74) *Attorney, Agent, or Firm* — Andrus, Sceales, Starke & Sawall, LLP

(57) ABSTRACT

A method of utilizing maternal-fetal monitoring system to monitor the physiological properties of both a maternal patient and a fetus. The method places a series of ECG electrodes across the maternal patient's abdomen and receives ECG input waveforms across a plurality of separate channels. The method processes the channels using an ICA algorithm to generate a series of ICA output waveforms. The ICA output waveforms are analyzed for each individual epoch to determine which of the channels include a maternal signal or a fetal signal source. Based upon the determination of which channel includes the fetal and maternal signals, further processing is carried out on the ICA output waveform on the identified channel to obtain physiological properties for the patient and the fetus. During the next epoch, the same signal processing occurs, such that the system can identify the fetal and maternal signals even as the fetal and maternal jump channels from one epoch to another.

17 Claims, 8 Drawing Sheets

METHOD OF FETAL AND MATERNAL ECG IDENTIFICATION ACROSS MULTIPLE EPOCHS

FIELD OF THE INVENTION

The present disclosure generally relates to a method of non-invasively monitoring the heartbeat and ECG of an unborn fetus. More specifically, the present disclosure relates to a method of determining maternal and fetal heart rates and selecting maternal and fetal ECG signals from an electrocardiogram (ECG) obtained from a maternal patient during continuous monitoring of the maternal patient.

BACKGROUND OF THE INVENTION

An electrocardiogram (ECG) is a very important tool in the diagnosis of heart disease and abnormalities in both children and adults. The new detection capabilities provided by recent advances in signal processing allow the possibility of obtaining valuable information from fetal heart electrical activity. The use of a fetal ECG (fECG) could lead to the early detection and monitoring of heart abnormalities providing better information throughout gestation and particularly perinatally.

However, obtaining an accurate fetal ECG is difficult due to the weaker fetal information obtained from the abdomen of the mother. Specifically, when multiple ECG electrodes are placed on the abdomen of the mother to gather the required ECG information, several obvious problems arise. The first is that the mother's ECG is present and is usually significantly larger than the ECG of the fetus. Second, if monitoring is being done late in pregnancy, uterine contractions may be present, which result in large electrical artifacts that obliterate or mask the fetal signal. Third, in many cases, the mother is experiencing discomfort and is unable to lie still, which creates large electrical muscle artifacts.

Presently, signal processing techniques exist, including the use of independent component analysis (ICA) algorithms, that are applied the input ECG signals obtained from the mother to provide clean waveforms that can be further processed. In many cases, the output from the ICA algorithm can be used to provide a signal for finding the fetal heart rate. Typically, one channel of the multi-channel abdominal maternal ECG leads is used for determining the fetal heart rate. The ICA algorithm is performed on a set of waveforms over an epoch having a determined length, such as 4 to 5 seconds. Although a particular channel from the ICA algorithm output can be used to identify fetal heart rate for the specific epoch, the fetal and maternal ECG signals oftentimes change channels from one epoch to the next. For the purposes of determining fetal heart rate, the channel jumping of the ICA output is a problem since a separated fECG signal may not be in the same waveform position from epoch to epoch. Additionally, automated techniques for identifying and monitoring the fetal ECG are further complicated by the changing channels of both the fetal and maternal signals over multiple epochs. Therefore, it becomes necessary to have a method and means to recognize which among the scrambled plurality of ICA output waveforms from any epoch is a fetal ECG, a maternal ECG, a uterine contraction or just noise. A need exists to make this determination for each epoch of a series of epochs such that the fetal ECG and maternal ECG can be monitored over an extended period of time.

BRIEF DESCRIPTION OF THE DISCLOSURE

The present disclosure generally relates to a method of monitoring maternal and fetal vital signs, including ECG and heart rate information, obtained from a maternal patient. More specifically, the present disclosure relates to a method of identifying which ICA channels derived from ECG signals from the maternal patient are produced by fetal and material ECG sources as the algorithms moves through a series of sequential epochs.

Initially, a plurality of ECG electrodes is placed on the abdomen of the maternal patient to obtain ECG signals from the maternal patient. The electrodes are connected to an acquisition system such that input ECG waveforms are detected and received for monitoring heart rate or other ECG properties.

Once the input waveforms are received at the ECG monitoring device, an independent component analysis (ICA) algorithm is applied to each of the waveforms separately over a defined epoch. Typically, the defined epoch is between 4 and 5 seconds in length such that the ICA algorithm is applied to the waveform over the entire duration of the epoch. The ICA algorithms are a group of well-known and widely available processing algorithms.

After processing through the ICA algorithm, an ICA output waveform is generated and associated with each of the plurality of channels. The ICA algorithm acts as a filtering and cleaning algorithm that enhances and identifies hidden independent sources from the original input waveforms from the ECG electrodes and generates more useful output waveforms. Usually, since the system and method utilizes a given number of channels, the ICA algorithm generates the same number of separate, individual ICA output waveforms.

Although ICA algorithms are readily available for processing input waveforms from each channel of an ECG reading taken from a patient, the present disclosure provides improved processing techniques for identifying which channels of the plurality of ICA output channels are fetal or maternal signal sources for the current epoch. Since the maternal and fetal ICA output signals can change channels from one epoch to the next, the system and method of the present disclosure operates to identify the channels that are either the maternal signal or the fetal signal for each individual epoch.

In accordance with a first method, a discrete Fourier transform (DFT) is computed using a fast Fourier transformer (FFT) for each ICA output waveform. The FFT algorithm is well known and will be used whenever a DFT is required for the methods being disclosed in the following. The FFT for each of the ICA output waveforms is classified and the significant frequency peaks and the location of such peaks are determined for the ICA output waveform for each of the plurality of channels.

Once all of the FFTs for the ICA output waveforms have been determined and the frequency peaks identified, the system compares the peaks of the FFT for each of the ICA output waveforms to a known, typical maternal signal determined from a previous epoch. If the frequency peaks match the maternal signal from the previous epoch, the ICA output waveform is classified as being a maternal signal and is stored for further processing.

If the system determines that the ICA output waveform being analyzed does not match the known maternal signal, the system then determines whether the FFT for the ICA output waveform matches a known fetal signal from a previous epoch. If the signal matches the known fetal signal from a previous epoch, the ICA output waveform is classified as being a fetal signal and is stored in memory for further processing.

If the system determines that a particular ICA output waveform does not match either a known maternal signal or a known fetal signal, the system can compare the FFT for the ICA output waveform to a known uterine signal. If the FFT for the ICA output waveform matches the known uterine signal, the waveform is stored as a waveform representing uterine activity.

If the ICA output waveform does not match the known maternal signal, the known fetal signal or the known uterine signal, the ICA output waveform is classified as noise.

Once the system determines which channels are fetal and the maternal in characteristics, the waveforms from these channels are fed to separate fetal and maternal ECG processors for analysis in a known manner. This method is carried out during each epoch such that the system and method identifies which ICA output waveforms are fetal or maternal for each epoch.

In an alternate method, the system and method of the present disclosure utilizes a correlation function to determine which ICA output channels are the fetal or maternal source signals. In this alternate approach, the system first obtains a fetal QRS template from some previous time, such as a previous epoch. Since a given fetal QRS template will most likely correlate with the QRS structure for a fetal source signal from an ICA output waveform of the present epoch, the system calculates a correlation of the known fetal QRS template through time across the waveforms of the current epoch. Since at least one channel is expected to be a fetal source signal, the correlation of the channel including the fetal properties will result in high correlation as the template aligns with the QRS of the ICA output waveform, which implies that there will be high correlation peaks spaced in a regular pattern if the particular ICA waveform is a fetal source signal. Based upon the ICA output signal that generates the best correlation, this ICA output waveform is identified as including the fetal signal. If the remaining ICA output waveform channels are not a fetal source signal, these channels will have a lower, more varied correlation signal and will not be classified as a fetal source signal.

In addition to utilizing a fetal QRS template, the system and method can utilize a maternal QRS template that is also determined from some previous time period, such as a previous epoch. Like the steps required to identify a fetal source signal, the system calculates a correlation for each of the ICA output waveforms and, based upon the correlation, determines which of the ICA output waveforms is a maternal source signal.

Once the system has determined which channels are maternal signals and fetal signals, the waveforms from these channels are directed to a fetal ECG processor and a maternal ECG processor for further processing and display of the ECG signal for both the patient and the fetus. The two methods discussed, namely the FFT and the correlation methods, each have their own advantages and disadvantages. The FFT technique requires no template, is capable of immediately identifying the fetal and maternal heart rates by noting the position of fundamental and harmonic peaks in the FFTs of the appropriate source signal waveforms, and allows easy frequency domain filtering to aid the system in heart rate calculations. On the other hand, the correlation technique aids in heart rate calculations by producing clear correlation peaks with the needed period, but requires a template that may not always be easily available.

DETAILED DESCRIPTION OF THE INVENTION

Figure 1:
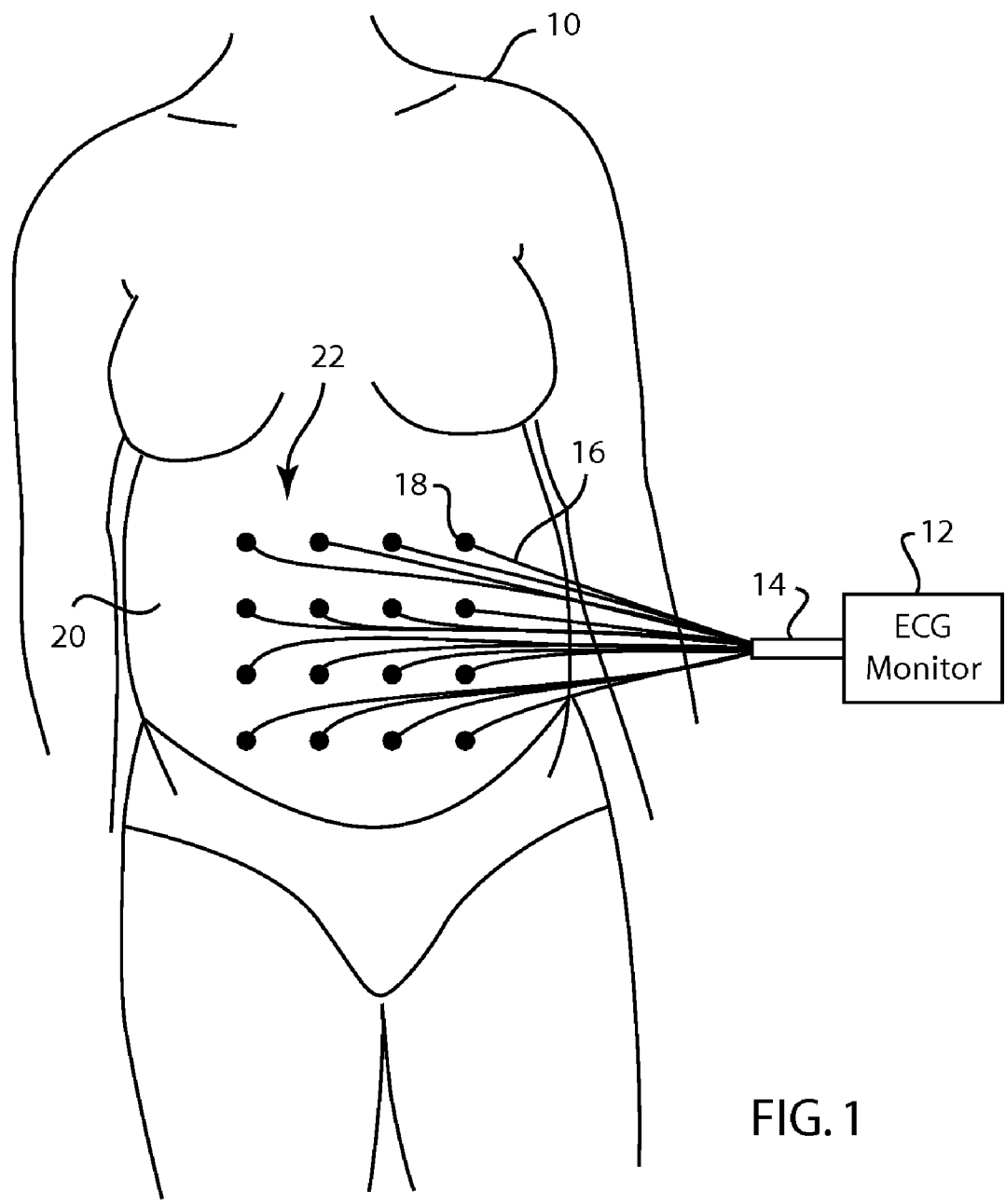
FIG. 1 is an illustration of a set of ECG electrodes positioned on an abdomen of a maternal patient in accordance with the present disclosure.

FIG. 1 illustrates a maternal patient 10 connected to an ECG monitor 12 such that the ECG monitor 12 can monitor both physiological data from the patient 10 as well as a fetus (not shown) being carried by the patient 10. As illustrated in FIG. 1, the ECG monitor receives a sensor cable 14 that includes individual channels or leads 16 each connected to an electrode 18 attached to the abdomen 20 of the patient 10. In the embodiment shown in FIG. 1, the sensor cable 14 includes sixteen separate ECG electrodes 18 that are positioned in an array 22 spaced on the mother's abdomen 20. In addition to the sixteen ECG electrodes 18, the sensor cable 14 can also include a ground electrode and a reference electrode, as is conventional when recording ECG measurements from a patient 10. Although the electrode placement shown in FIG. 1 is in a general four-by-four array, various other electrode arrangements can be utilized while operating within the scope of the present disclosure.

In order to achieve good separation, the abdominal ECG electrodes 18 should not be placed too close together and should involve a wide coverage of the abdomen. Typically, the regularly spaced sixteen electrodes are spaced over the entire skin surface of the patient 10. Each of the ECG electrodes 18 detects electrical signals present on the skin of the patient and returns the sensed electrical signals to the ECG monitor 12 over the series of separate patient leads 16.

As will be described in much greater detail below, the ECG monitor 12 receives a set of multiple input waveforms from the ECG electrodes 18. The ECG monitor 12 includes operating programs and software, to be described in much greater detail below, that operate to separate ECG and physiological information relating to the mother from ECG information and physiological parameters resulting from the fetus. As used throughout the remaining portions of this disclosure, the physiological information that may be derived for both the mother and the fetus include at least maternal and fetal heart rate, and may include maternal respiratory rate, other maternal and fetal ECG characteristics and the electrohistogram (EHG).

Figure 2:
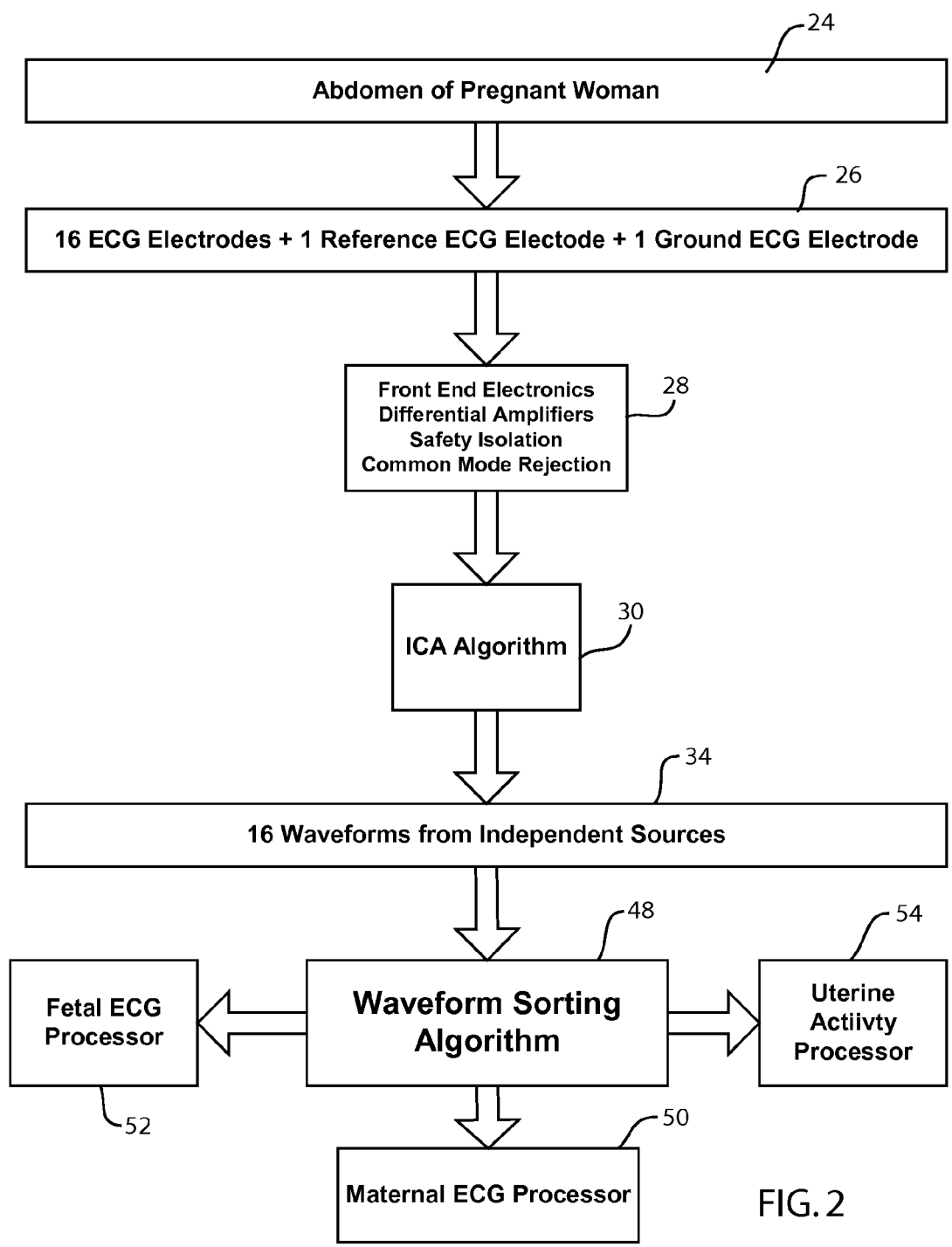
FIG. 2 is a data flow diagram of the method of the disclosure that utilizes an ICA algorithm applied to fetal ECG extraction.

Referring now to FIG. 2, the initial step in the method of the present disclosure is to prepare the abdomen of a pregnant patient for the application of the array of electrodes, as illustrated in step 24. This preparation typically includes removing clothing covering the abdomen 20 and cleaning the abdomen to prepare the skin for good surface contact with the individual ECG electrodes 18, as shown in FIG. 1. Referring back to FIG. 2, the next step in the method is to place the sixteen ECG electrodes, the one reference ECG electrode and the one ground ECG electrode on the patient, as set forth in step 26. Typically, each of the electrodes adheres to the patient's abdomen and creates the required low impedance skin to electrode contact to sense electrical signals present on the surface of the patient due to electrical activity within both the patient and the fetus.

Once the individual electrodes 18 are placed on the patient's abdomen 20, sixteen separate, individual input waveforms are received at the ECG monitor through the sixteen leads 16 shown in FIG. 1. As shown in step 28 of FIG. 2, the ECG monitor 12 includes front end electronics, differential amplifiers, isolation devices and common mode rejection components that receive the individual input waveforms from the electrodes and provide for initial processing of the sixteen separate input waveforms received on the sixteen separate channels at the ECG monitor 12. Preferably, the ECG monitor includes computing and storage means for receiving the individual input waveforms and outputting monitoring data for use by a physician. Such digital instrumentation, as is well understood by skilled artisans, can process the input waveforms by applying algorithms and filtering operations. Further, the computing means can include storage components for recording the input waveforms, as will be described in detail below. In the embodiment of the disclosure shown, the ECG monitor 12 provides initial processing of the input waveforms received across the sixteen separate channels and records the input waveform in memory contained within the ECG monitor. Since the waveform for each channel is received continuously at the ECG monitor, the ECG monitor 12 stores the input waveforms continuously in a memory device contained within the ECG monitor.

As described previously, the input waveforms obtained from the sixteen channels connected to the ECG monitor 12 include a large amount of noise and unwanted signal information. To remove artifacts and separate the desired information from the maternal and fetal sources in the input waveforms obtained directly from the ECG electrodes, the system and method shown in FIG. 2 utilizes blind source separation (BSS) using an independent component analysis (ICA) algorithm applied to the sixteen separate channels from the individual electrodes applied to the patient's abdomen. To apply the ICA algorithm shown in step 30, the ECG monitor stores the continuous input waveforms from each of the sixteen channels over a defined period of time.

The stored input waveforms for each of the sixteen channels connected to the ECG electrodes are stored and segmented into individual epochs. Typically, an epoch has a fixed duration such that signal processing techniques can be carried out on each of the individual waveforms over the epoch. In the embodiment shown in the present disclosure, an epoch typically has a duration of approximately 4-5 seconds, although other durations are contemplated. It is preferred that each epoch have a duration that is greater than the heartbeat period for both the patient 10 and the fetus. An epoch duration of 5 seconds is shown in the embodiment of the present disclosure, as illustrated by the epoch duration 32 shown in FIG. 3.

Referring back to FIG. 2, the ICA algorithm is applied to the set of the input waveforms at step 30 to generate clean and separated signals that represent the electrical activity of the mother, the fetus and any other independent sources that may be present during the acquisition of the sixteen ECG channels 18. The BSS/ICA data processing techniques of step 30 are well known to those of skill in the art and are readily available from numerous outlets or can be developed and optimized for an intended purpose. The ICA algorithm of step 30 is preferably implemented in real time on a computing means contained within the ECG monitor. The ICA algorithm filters the input waveforms obtained directly from the ECG electrodes such that the filtered waveforms can be easily further processed by other components. As described, ICA algorithms are well known and have been used for quite some time. As an example, the ICA algorithm could be any known algorithm such as FASTICA or CUBICA, although other types of ICA algorithms are contemplated as being within the scope of the present disclosure.

Since each of the input waveforms is received on a separate channel from a separate ECG electrode, the ICA algorithm 30 generates sixteen separate waveforms that are each related to separate, independent sources, as indicated in step 34. Since the ICA algorithm 30 filters and removes much of the noise from the input waveforms, the sixteen ICA output waveforms, generated in step 34, can be utilized to determine on which channel the fetal and maternal heart rate and ECG signals are present. Once the channels have been identified, further processing can be conducted on the maternal and fetal signals.

Figure 3:
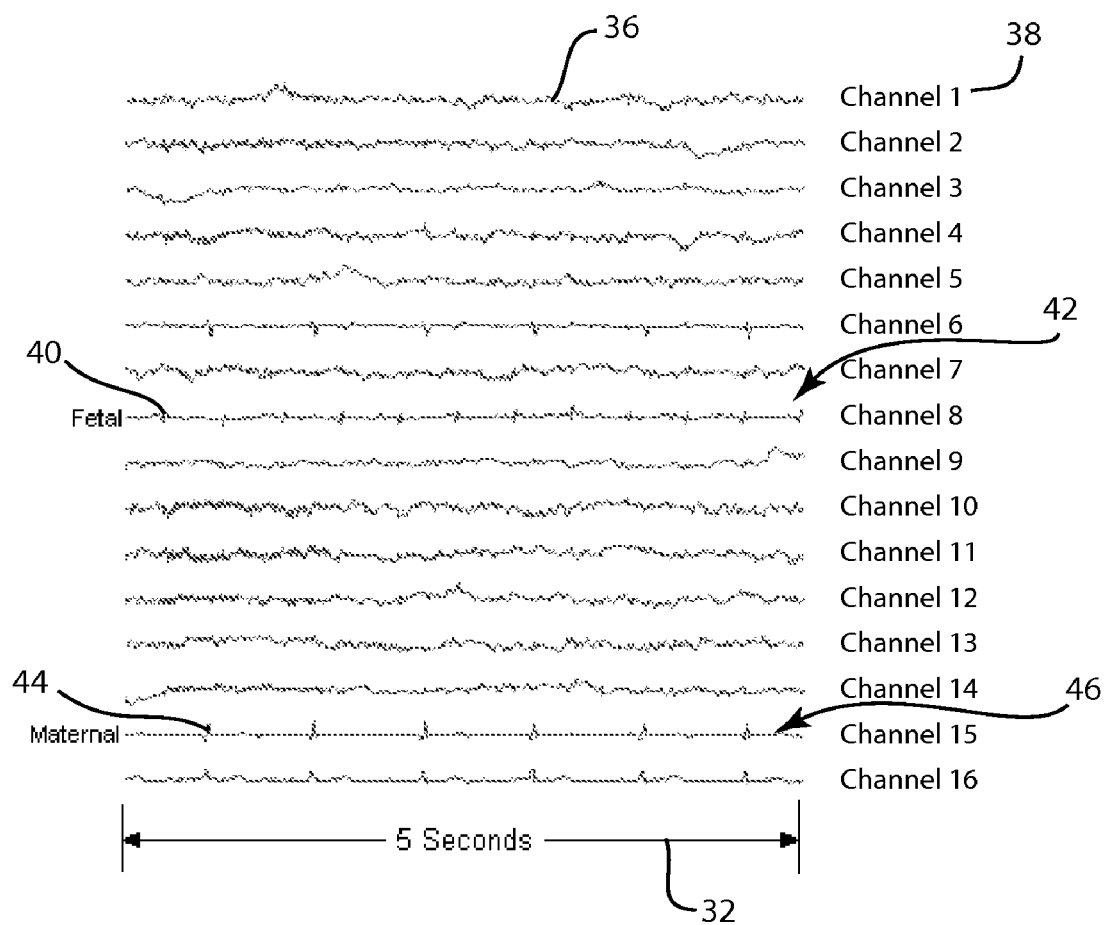
FIG. 3 is an example of ICA output waveforms from electrodes applied to a maternal abdomen.

Referring now to FIG. 3, thereshown are the ICA output waveforms 36 that are generated from the ICA algorithm shown in step 30 of FIG. 2. The ICA output waveforms 36 are present along each of the sixteen channels 38, where each channel 38 represents one of the plurality of waveforms obtained from the electrodes placed on the patient's abdomen. As can be seen in FIG. 3, many of the sixteen channels 38 shown in FIG. 3 include ICA output waveforms that appear to present only noise or signals having very little usefulness in monitoring the fetal and maternal ECGs and heart rates. However, as shown in the specific embodiment of FIG. 3, the ICA output waveform on channel 8 includes a series of signature QRS events 40 that represent the heartbeat and ECG signal from the fetus. Thus, the fetal signal 42 for the epoch 32 is said to reside on channel 8.

Likewise, channel 15 includes a series of QRS events 42 that represent the heart rate and ECG signal received from the maternal patient. Thus, channel 15 from the epoch 32 includes the maternal signal 46. In addition to the QRS events 44, the material signal 46 also includes T-waves following the application of the ICA algorithm.

As can be understood in the plurality of ICA output waveforms shown in FIG. 3, the ICA output waveforms 36 can be utilized to determine significant physiological properties for both the patient and the fetus. Specifically, the ICA output waveform 36 present on channel 15 can be utilized to determine physiological properties from the maternal patient, while the ICA output waveform present on channel 8 can be utilized to determine physiological properties for the fetus. This use of the ICA algorithm to generate the ICA output waveforms shown in FIG. 3 is generally well known and defined in the state of the art.

However, as described previously, the fetal signal 42 and the maternal signal 46 can, and typically do, change channels from one epoch to another, such that although the maternal and fetal signals may be determined for a first epoch, the maternal and fetal signals for the next epoch could be located on different channels. Thus, when utilizing an automated technique for determining physiological parameters from the patient based upon ECG information, the channel including both the fetal signal 42 and the maternal signal 46 must be known, which presents a significant challenge addressed by the present disclosure.

Referring back to FIG. 2, the next step in the method of the present disclosure is to utilize some type of waveform sorting algorithm 48 to identify which channels include the maternal source signal and the fetal source signal. Once the waveform sorting algorithm 48 determines which channels include the maternal and fetal signals, the information from these channels are fed to either a maternal ECG processor 50 or a fetal ECG processor 52 for further processing. The maternal ECG processor 50 can determine physiological properties for the maternal patient based upon analysis of the ICA output waveform that includes the maternal signal, while the fetal ECG processor 52 can perform processing techniques to generate physiological properties for the fetus. In addition to the maternal and fetal ECG processors 50, 52, the system can also include a uterine activity processor 54 that can be used to monitor the uterine activity of the patient, such as contraction strength, contraction intervals and other relevant information from the maternal patient during the contractions preceding the delivery of the fetus.

As described above, one significant problem that arises by utilizing only the ICA algorithm 30 to determine which channel includes a fetal signal and a maternal signal is that, although the location of these signals can be determined for a selected epoch, the location of these signals may change from one epoch to the next. Thus, at least two alternative ways of deciding which signals are on which channels have been developed in accordance with the present disclosure.

Figure 10:
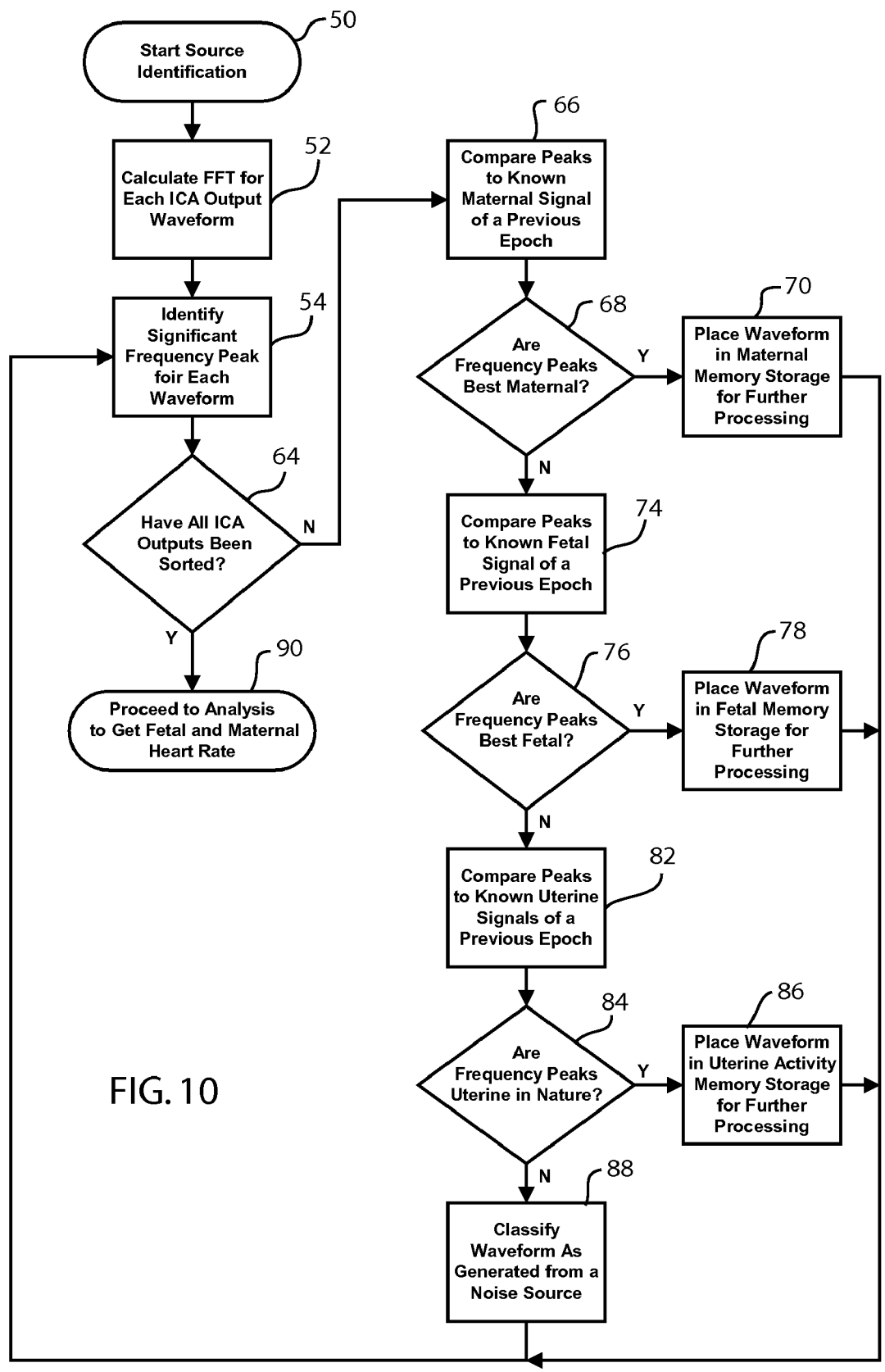
FIG. 10 is a flowchart illustrating the steps to determine whether a waveform includes the fetal signal or the maternal signal using frequency content.

The first method of deciding which channels include the maternal signal and the fetal signal is generally shown and described in the flowchart of FIG. 10. As indicated in FIG. 10, once the sixteen separate, independent ICA output waveforms have been generated, the system begins the process of identifying the waveforms in step 51. Once the source identification process has begun, the method first calculates a fast Fourier transform (FFT) for each of the ICA output waveforms, as shown in step 53. In the process shown in FIG. 10, the method calculates each of the ICA waveforms sequentially from channel 1 to channel 16, as will be described.

Figure 4:
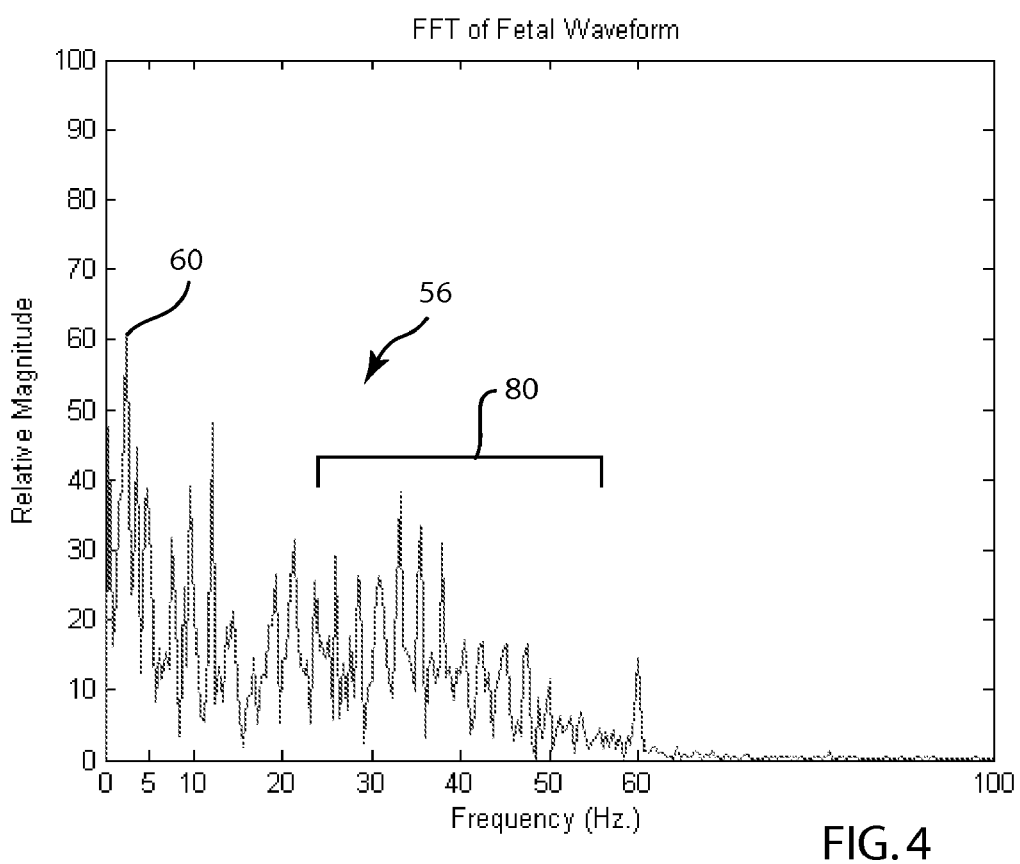
FIG. 4 is an example of the frequency content of a fetal waveform after an FFT.
Figure 5:
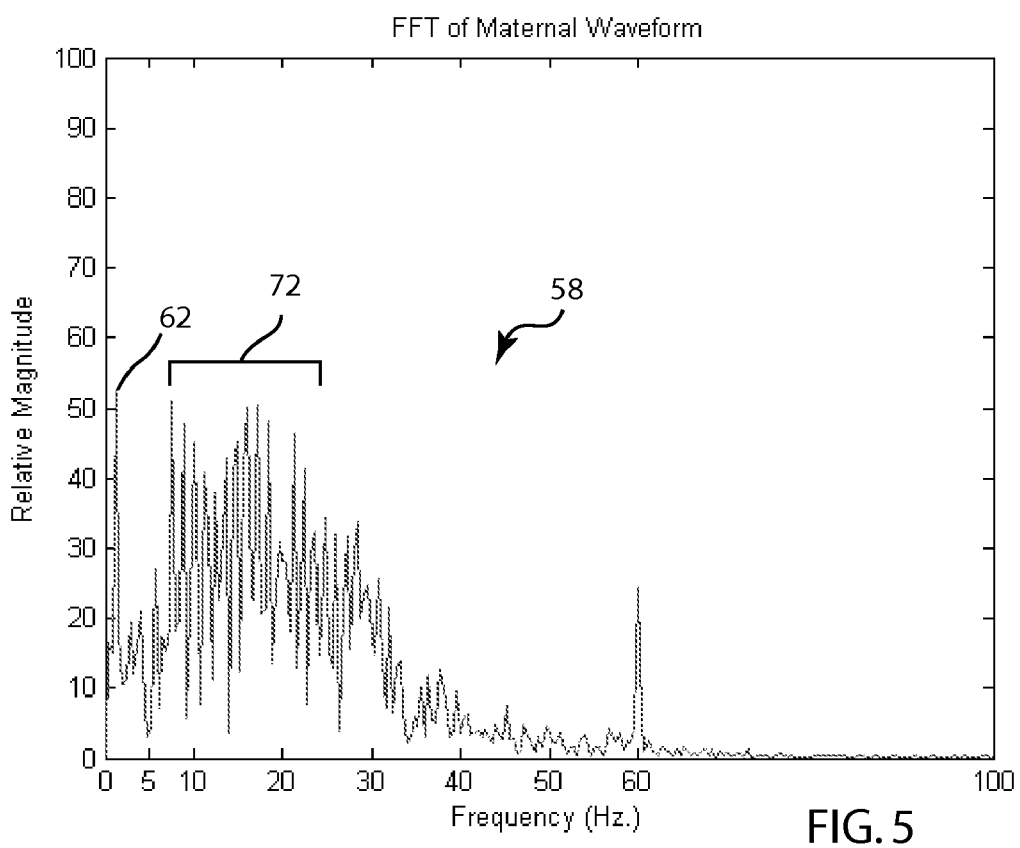
FIG. 5 is an example of the frequency content of a maternal waveform following an FFT.

Once the FFT for each of the ICA output waveforms have been calculated, the system identifies significant frequency peaks for each waveform in step 55. FIGS. 4 and 5 illustrate the FFT of a fetal waveform 56 and an FFT for a maternal waveform 58. Although FIGS. 4 and 5 illustrate the FFT for the fetal waveform and the maternal waveform, it should be understood that the FFT for ICA output waveforms that include neither the fetal waveform nor the maternal waveform present a different energy characteristic than those shown in FIGS. 4 and 5.

As illustrated in FIG. 4, the first peak 60 for the fetal waveform represents the fetal heart rate for the fetus. In the embodiment shown in FIG. 4, the peak 60 occurs at approximately 2.5 Hz, which is representative of the heart rate of the fetus. Likewise, the maternal waveform 58 shown in FIG. 5 also includes a peak 62 that represents the maternal heart rate. In the embodiment shown in FIG. 5, the peak 62 occurs at approximately 1.5 Hz, which is representative of the fundamental heart rate of the maternal patient.

Referring back to FIG. 10, once the significant frequency peaks for each waveform have been identified in step 54, the system determines whether all of the ICA output waveforms have been sorted in step 64. If not all of the ICA output waveforms have been sorted, the system proceeds to step 66 and attempts to classify the FFT based upon the ICA output waveform from the current channel being analyzed. In step 66, the system compares the energy peaks identified in step 55 to peaks that are present in a typical maternal signal calculated from a previous epoch or previously stored in a memory location. If the system determines in step 68 that the frequency peaks of the FFT waveform being analyzed correspond to a maternal signal, the system places the waveform in a maternal memory storage location for further processing, as indicated in step 70.

Referring back to FIG. 5, for a maternal waveform, a significant number of energy peaks occur within the frequency range 72 which, in the embodiment shown, occurs approximately between 10-20 Hz. Since the waveform 58 includes a significant amount of energy and peaks within the frequency range 72, the waveform 58 shown in FIG. 5 is classified by the present method as a maternal waveform. In contrast to the waveform shown in FIG. 5, the waveform 56 shown in FIG. 4 does not include many peaks within the frequency range of 10-20 Hz. Thus, the waveform 56 shown in FIG. 4 is clearly not a maternal waveform. Note that it is expected that a fetal ECG signal will contain faster components, i.e. higher energy at higher harmonic frequencies, than the maternal ECG signal.

Referring back to FIG. 10, when the system determines in step 68 that the frequency peaks are not maternal, the system then compares the frequency peaks to a typical fetal signal determined from a previous epoch, in step 74. Based upon the comparison in step 74, the system determines in step 76 whether the frequency peaks match the typical fetal signal. If the frequency peaks match the typical fetal signal, the system places the waveform in a memory storage for further processing, as shown in step 78.

Referring now to FIG. 4, the waveform 56 shown in FIG. 4 has a significant amount of energy and peaks within the frequency range 80, which is typically representative of a fetal waveform. In the embodiment shown, the frequency range 80 is approximately 20-50 Hz. As a comparison, the waveform 58 shown in FIG. 5 includes a very small amount of energy in the frequency range between 20-50 Hz, which indicates that the waveform 58 is not a fetal waveform but, as previously described, the waveform 58 corresponds to a maternal waveform.

If the system determines in step 76 that the frequency peaks are not fetal, the system then compares the peaks to typical uterine signals determined from a previous epoch, as indicated in step 82. The typical uterine signals from the previous epoch are due to contractions of the patient's abdominal muscles, such as during a contraction. If the frequency peaks are classified as uterine in nature in step 84, the system places the waveform in memory for further processing in step 86. However, if the system determines that the frequency peaks are not maternal, fetal or uterine in nature, the system classifies the waveform as noise, as indicated in step 88. Once the FFT for the ICA output waveform on the specific channel is classified, the system returns to step 54 to identify the significant frequency peaks for the next waveform on the next channel. Once all of the ICA waveforms have been sorted, the system proceeds to step 90 and determines the fetal and maternal heart rate information based upon the knowledge of which channel is a fetal signal and which channel is a maternal signal, as determined in the previous analysis.

As discussed above, once the system determines which channels of the plurality of channels are fetal and which are maternal, the fetal and maternal signals are sent to their respective fetal ECG processor 52 and maternal ECG processor 50, as shown in FIG. 2. The method illustrated in FIG. 10 allows the system to determine which channels are fetal or maternal in characteristics so that additional processing can be performed in a manner well known to those of ordinary skill in the art.

As can be understood by the above disclosure, the system determines which channels are fetal and maternal signals based upon an analysis and comparison of an FFT for each ICA output waveform. For example, the peaks in the FFT that were known from the previous epoch for a maternal signal and fetal signal would be expected to be present for a newly obtained epoch. Additionally, an FFT peak is expected in the neighborhood of a known heart rate for either a maternal or fetal signal, which can help distinguish the proper classification of signals. Once the waveforms for the current epoch are analyzed, the system saves the waveform for the maternal and fetal signals in memory such that the saved signals may be utilized when analyzing the ICA output waveforms for the next epoch. In this manner, the system and method of the present disclosure utilizes information from the most recent epoch to classify signals for the current epoch.

Figure 6:
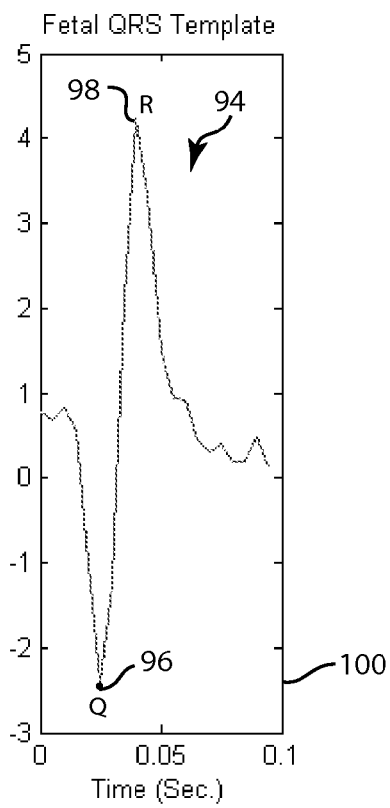
FIG. 6 is a sample fetal QRS template.

As an alternate method to the method of utilizing an FFT for each waveform described above, the system can also utilize a correlation method to classify which channels of the ICA output waveforms are the fetal source signals or the maternal source signals. Algorithms for calculating correlations are well known by those skilled in the art and are essentially a measure of the agreement of the waveform pattern between two input signals. For the purposes described here the correlation algorithm requires a known template as one of the inputs. Using a time interval around some benchmark event such as a QRS event or a uterine contraction event can specify the template for use in the correlation calculation, but other means can be used to find an appropriate template. The method of determining which channels include the fetal and maternal signals will now be described with reference to the flowchart of FIG. 11. Initially, the system starts the identification process in step 92. After starting the process in step 92, the system obtains a fetal QRS template from a previous time period or a previous epoch, as illustrated in step 93. As illustrated in FIG. 6, the fetal QRS template 94 defines a QRS episode that includes a Q peak 96 and an R peak 98 over a time duration 100. Preferably, the QRS template 94 is determined during a previous epoch based upon the identification of which ICA output waveform includes the fetal signal.

Referring back to FIG. 11, once the QRS template has been determined, the system calculates a correlation for each of the ICA output waveforms based upon the QRS template 94, as illustrated in step 102. The correlation of the ICA output waveform on each channel of the plurality of channels with the fetal QRS template 94 from a previous epoch will result in the waveform not having a high correlation if the waveform does not include the fetal signal, while the QRS template, when run across a waveform including the fetal signal, will give high correlation peaks with the period of the fetal heart rate. Thus, the waveform that generates high correlation peaks will be the waveform that is a fetal source signal, while those waveforms that result in low correlation will be waveforms that do not include fetal components.

Figure 7:
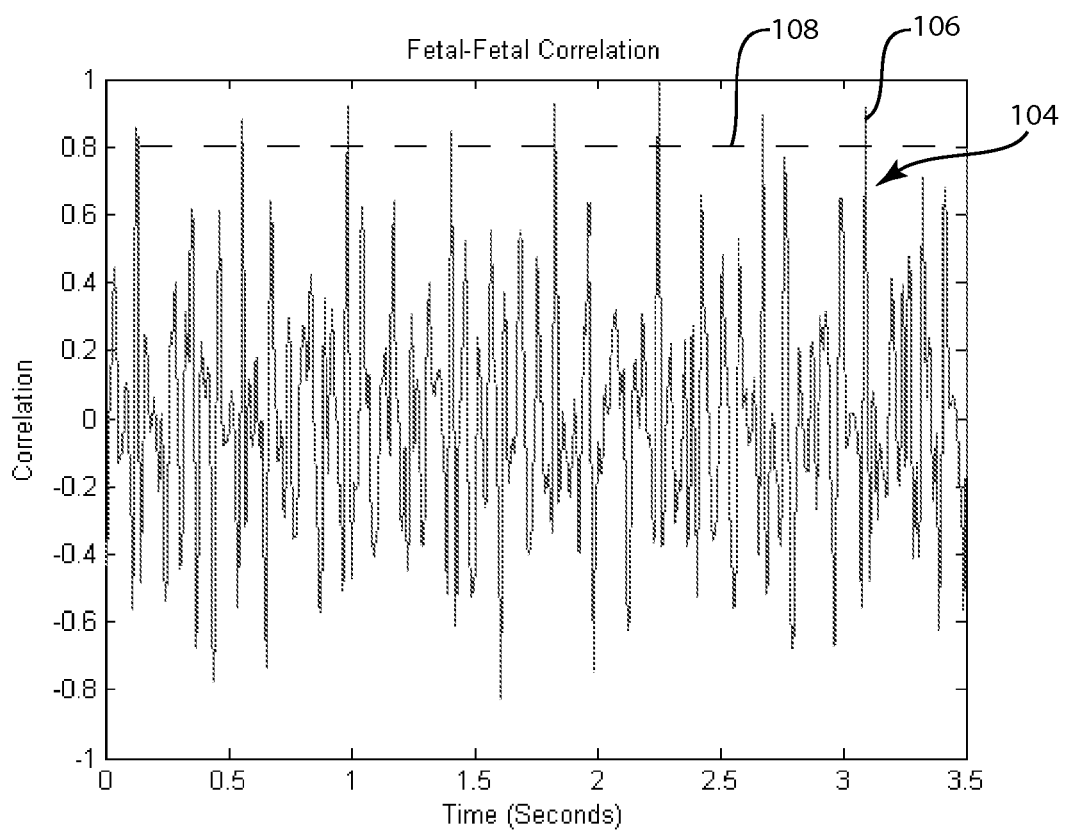
FIG. 7 is an example correlation output using the fetal QRS template on a fetal ICA output waveform.

Referring now to FIG. 7, thereshown is the correlation of the fetal QRS template to an ICA output waveform that, based upon the correlation results, includes the fetal signal. As indicated in FIG. 7, the correlation signal 104 includes a number of peaks 106 that extend above a correlation baseline 108. As is known, when the correlation waveform approaches 1, there is almost an identical correlation between the QRS template and the signal being analyzed. In the embodiment shown in FIG. 7, the threshold 108 is positioned at a correlation of 0.8, which indicates a high degree of correlation between the template and the signal being analyzed. As indicated in FIG. 7, the correlation signal 104 includes numerous periodic peaks 106 that extend above the threshold 108. Thus, the correlation signal 104 shown in FIG. 7 has a very high correlation, indicating that the channel being analyzed is fetal in its characteristics.

Figure 8:
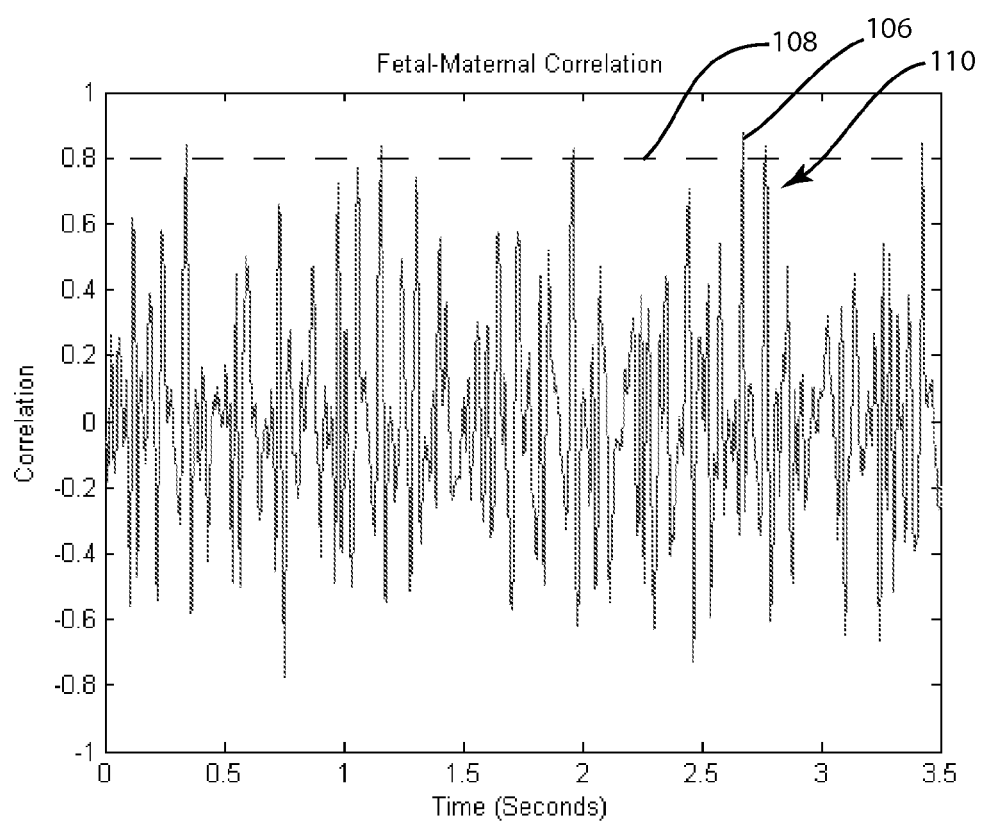
FIG. 8 is an example correlation output utilizing the fetal QRS template on a maternal waveform.

Referring now to FIG. 8, thereshown is a correlation signal 110 for a different channel than shown in FIG. 7. As indicated in FIG. 8, only a few peaks 106 extend above the threshold 108 and, of those peaks that extend above the threshold, each peak 106 extends only slightly above the threshold. Thus, when comparing the two correlation signals 104 and 110, the correlation signal 104 clearly indicates a fetal signal, while the correlation signal 110 shown in FIG. 8 does not include the fetal signal. Based upon further signal processing, the ICA output waveform on the channel shown in FIG. 8 was determined to be a maternal signal. Thus, the correlation signal 110 shown in FIG. 8 does not represent the fetal signal, but instead represents the maternal signal.

Figure 9:
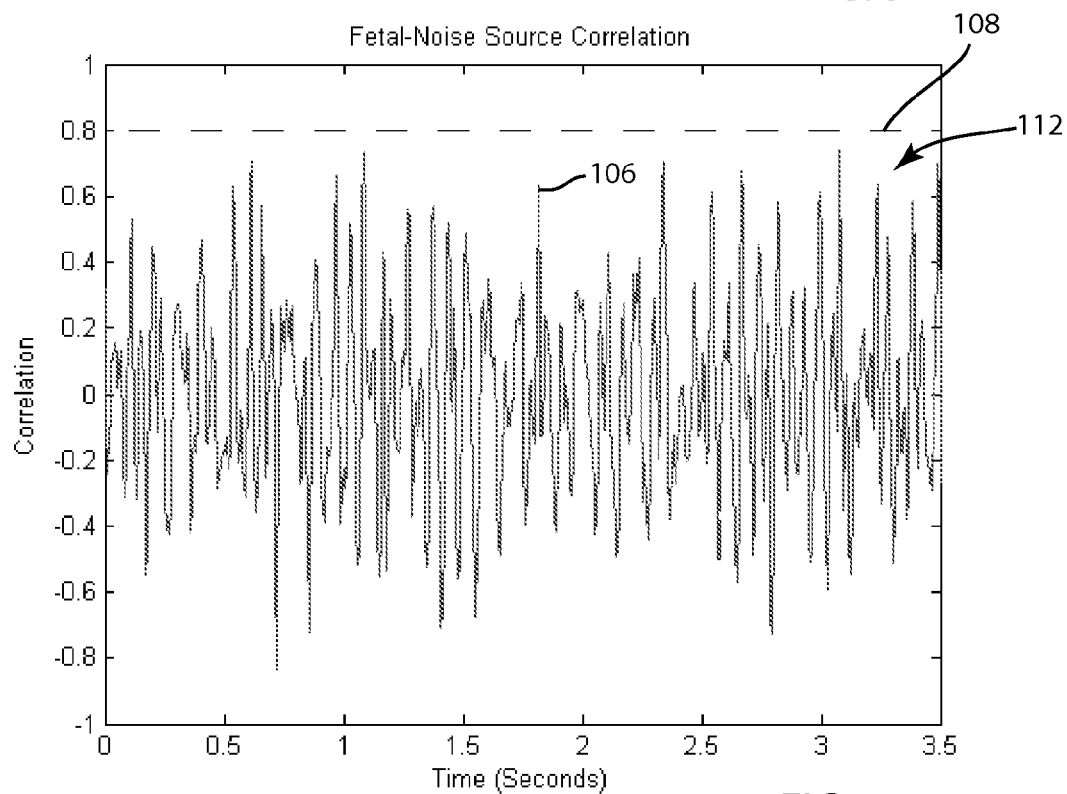
FIG. 9 is an example correlation output utilizing a fetal QRS template on a noise separated waveform.

FIG. 9 shows the correlation signal 112 for an ICA output waveform on yet another channel that represents noise. As clearly shown, none of the peaks 106 reach the threshold 108 such that the ICA output waveform on the channel being analyzed clearly does not include the fetal signal.

Referring back to FIG. 11, the system determines in step 114 whether all of the waveforms on all of the channels have been evaluated. If not all of the waveforms have been evaluated, the system picks a channel in step 116 and evaluates the waveform correlation. If the correlation signal for the channel has the highest appropriately spaced peaks, as determined in step 118, the system determines that the channel includes the fetal signal and places the ICA output waveform in memory storage for further processing, as indicated in step 120. However, if the waveform does not have the appropriately spaced peaks, the system returns to step 114 and continues to analyze each channel to determine which of the channels includes the fetal signal. The method shown in FIG. 11 is operable to determine which of the channels includes the fetal signal based upon a correlation between the ICA output waveforms and the fetal QRS template shown in FIG. 6.

Although the correlation method was described as identifying which channel includes the fetal signal, a similar method is carried out utilizing a maternal QRS template to determine which of the channels includes the maternal signal. In such procedure, the system generates a correlation of the ICA output waveform for each channel relative to the maternal QRS template. Based upon which channel includes the highest and appropriately spaced peaks, the system determines which channel includes the maternal signal. Similar steps can be carried out to determine which channel includes signals related to uterine activity.

Once the system and method determines which channels include the maternal signal, the fetal signal and the uterine signal, the system proceeds to step 122. At step 122, which corresponds to step 48 in FIG. 2, the system then transfers the ICA output waveforms from the required channels to the fetal ECG processor 52, the maternal ECG processor 50 and the uterine activity processor 54 for additional analysis.

Figure 11:
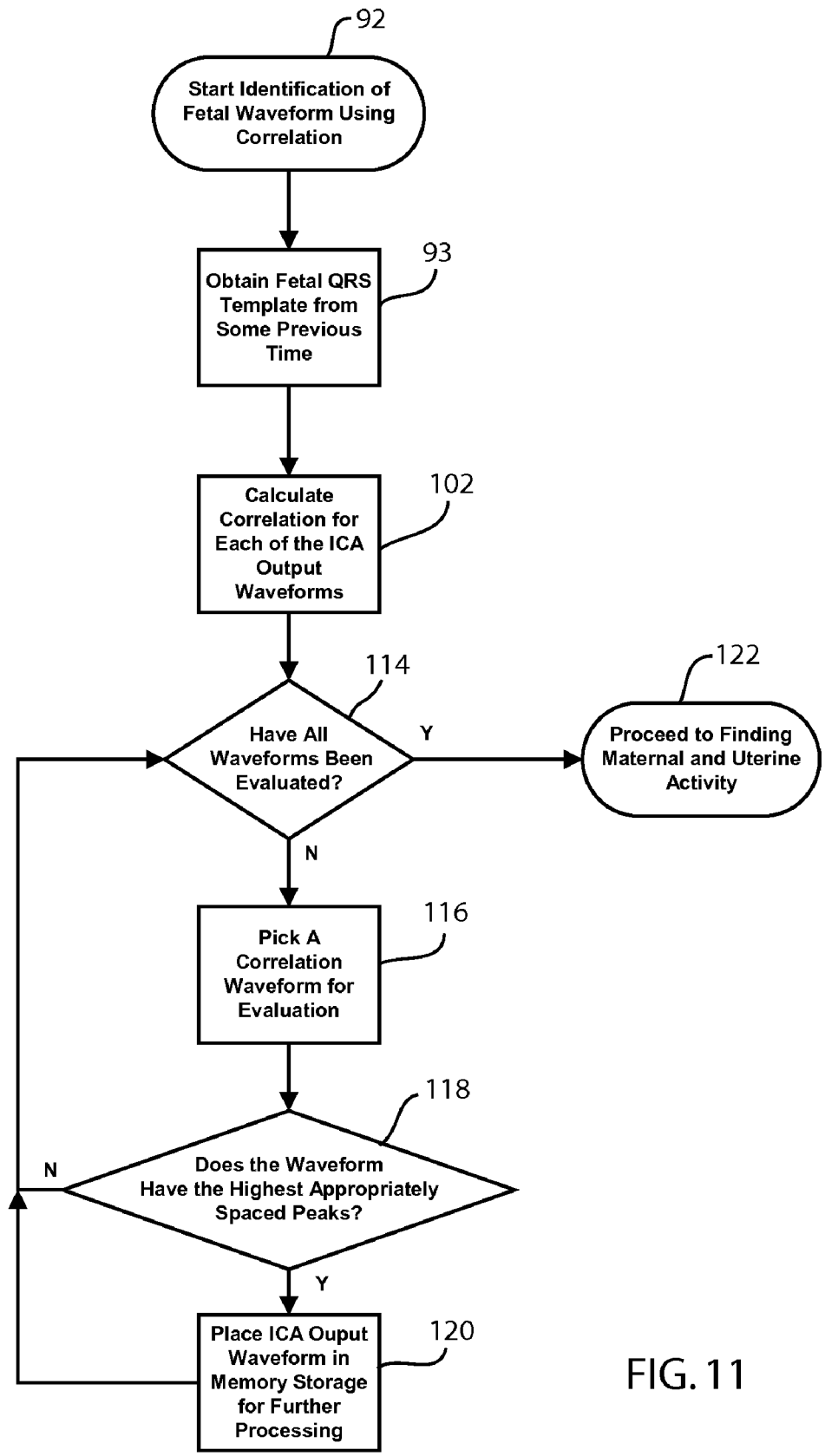
FIG. 11 is a flowchart for deciding whether a waveform includes the fetal signal utilizing a correlation analysis technique.

As can be understood by the above description, the method in FIG. 11 relies upon a fetal QRS template that was obtained from a previous epoch. Likewise, a maternal QRS template from a previous epoch is utilized to identify which processing channel includes the maternal signal. As can be understood by the above description, an issue arises when the first epoch is being analyzed by the system and method of the present disclosure. On the first epoch, a decision must be made as to which waveforms are fetal, maternal, uterine, muscle artifacts or some other artifact, since the QRS template from a past epoch is not available. Once this determination is made, the system can utilize the QRS template from the past epoch to carry out the method described. The initial decision as to which channel includes the various signals can be based upon other criteria, such as the rate at which the QRS's occur, the frequency content of the QRS complexes, the amplitude of the signal, and the general frequency content of the signals. As an example, the fetal QRS complex is typically known to have a slightly higher frequency content than the maternal QRS and the fetal heart rates are higher than maternal heart rates. It should be understood that various different methods to generate the first determination of which channel includes the maternal and fetal signals can be utilized while operating within the scope of the present disclosure. Once the first fetal and maternal signals have been determined, the system can utilize the methods described above to continue to monitor which channel includes the maternal signal and the fetal signal.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring maternal and fetal vital signs of a maternal patient and a fetus, the method comprising the steps of:
    placing a plurality of electrodes on the abdomen of the maternal patient;
    obtaining a plurality of separate input waveforms from the maternal patient through the plurality of electrodes over a predetermined epoch;
    conducting an independent component analysis (ICA) on the input waveforms over the epoch to generate a plurality of ICA output waveforms, wherein the ICA on the input waveforms is conducting for each epoch of a series of sequential epochs;
    determining which of the ICA output waveforms is generated from a maternal signal source and which of the ICA output waveforms is generated from a fetal signal source independently for each epoch of the series of sequential of epochs;
    processing the ICA output waveform that includes a maternal ECG signal to generate physiological information for the maternal patient; and
    processing the ICA output waveform that includes a fetal ECG signal to generate physiological information for the fetus.

2. The method of claim 1 wherein the step of determining which ICA output waveform includes the maternal ECG signal and which ICA output waveform includes the fetal ECG signal comprises:
    calculating a discrete Fourier transform (DFT) for each of the ICA output waveforms;
    identifying energy peaks in each of the DFTs;
    comparing the energy peaks in each of the DFTs to a typical profile for the maternal signal and a typical profile for the fetal signal; and
    selecting the ICA output waveform that most closely corresponds to the typical profile for the maternal ECG signal and the fetal ECG signal.

3. The method of claim 2 wherein the typical profile for the maternal ECG signal and the typical profile for the fetal ECG signal are based upon DFTs for the maternal ECG signal and the fetal ECG signal from a previous epoch.

4. The method of claim 2 further comprising the steps of:
    storing the ICA waveform that most closely corresponds to the typical profile for the maternal ECG signal in memory;
    storing the ICA waveform that most closely corresponds to the typical profile for the fetal ECG signal in memory; and
    utilizing the stored ICA waveforms to generate the physiological information of the patient and the fetus.

5. The method of claim 2 further comprising the steps of:
    detecting which of the ICA output waveforms includes a uterine activity signal; and processing the ICA output waveform that includes the uterine activity signal to generate information on uterine contraction.

6. The method of claim 5 wherein the step of determining which ICA output waveform includes the uterine activity signal comprises:
    comparing energy peaks for the DFT for each ICA output waveform to energy peaks determined from the uterine activity signal from a previous epoch; and
    selecting the ICA output waveform that most closely corresponds to the known uterine activity signal.

7. The method of claim 1 wherein the predetermined epoch has a duration greater than a duration between maternal patient heartbeats.

8. The method of claim 1 wherein the physiological information derived from the maternal patient and the fetus includes at least heart rates.

9. A method of monitoring maternal and fetal vital signs of a maternal patient and a fetus, the method comprising the steps of:
    placing a plurality of electrodes on the abdomen of the maternal patient;
    obtaining a plurality of separate input waveforms from the maternal patient through the plurality of electrodes over a predetermined epoch;
    conducting an independent component analysis (ICA) on the input waveforms for the current epoch to generate a plurality of ICA output waveforms;
    determining a template based upon a benchmark event from one of the previous epochs;
    determining which of the ICA output waveforms includes a fetal ECG signal based upon a comparison to the template;
    processing the ICA output waveform that includes the fetal ECG signal to generate physiological information for the fetus; and
    determining a second template using a second benchmark event from one of the previous epochs;
    determining which of the ICA output waveforms includes a maternal ECG signal based upon a comparison to the second template; and
    processing the ICA output waveform that includes the maternal ECG signal to generate physiological information for the maternal patient.

10. The method of claim 9 wherein the template comprises a known QRS episode from the ICA output waveform that includes the fetal ECG signal from one of the previous epochs.

11. The method of claim 10 wherein the step of determining which of the ICA output waveforms includes a fetal ECG signal for the current epoch comprises:
    correlating the known QRS episode with each of the ICA output waveforms; and selecting the ICA output waveform that includes the highest periodic correlation output as the ICA output waveform that contains the fetal ECG signal.

12. The method of claim 9 wherein the second template comprises a known maternal QRS episode for the ICA output waveform that came from the maternal ECG signal from the previous epoch.

13. The method of claim 12 wherein the step of determining which of the ICA output waveforms includes the maternal ECG signal for the current epoch comprises:
 correlating the known maternal QRS episode with each of the ICA output waveforms; and
 selecting the ICA output waveform that includes the highest correlation as the ICA output waveforms that includes the maternal ECG signal.

14. The method of claim 9 further comprising the step of updating the benchmark event and the associated template episode based upon the current epoch.

15. The method of claim 9 wherein the benchmark event includes a benchmark event for both the fetal ECG signal and a maternal ECG signal.

16. The method of claim 9 further comprising the steps of:
 storing the ICA output waveform that produces the highest periodic correlation result; and
 utilizing the stored ICA output waveform to generate the physiological information of the fetus.

17. The method of claim 9 further comprising the steps of:
 storing the ICA output waveform that produces the highest periodic correlation result; and
 utilizing the stored ICA output waveform to generate the physiological information of the maternal patient.

* * * * *